US009833390B2

(12) United States Patent
Homola et al.

(10) Patent No.: US 9,833,390 B2
(45) Date of Patent: Dec. 5, 2017

(54) DENTAL DEVICE FOR INHIBITION OF PLAQUE, CALCULUS AND GINGIVITIS

(71) Applicant: ProVSeal LLC, Reno, NV (US)

(72) Inventors: Andrew M. Homola, Naples, FL (US); Gary Pitts, Colorado Springs, CO (US); Ronald K. Dunton, Burlington, WA (US)

(73) Assignee: ProVSeal LLC, Reno, NV (US)

( * ) Notice: Subject to any disclaimer, the term of this patent is extended or adjusted under 35 U.S.C. 154(b) by 0 days.

(21) Appl. No.: 14/824,438

(22) Filed: Aug. 12, 2015

(65) Prior Publication Data

US 2017/0042773 A1    Feb. 16, 2017

(51) Int. Cl.
| | |
|---|---|
| *A61K 8/55* | (2006.01) |
| *A61Q 11/00* | (2006.01) |
| *A61K 8/92* | (2006.01) |
| *A61K 8/02* | (2006.01) |
| *A23K 20/00* | (2016.01) |
| *A23K 20/158* | (2016.01) |
| *A23K 20/10* | (2016.01) |
| *A23K 50/42* | (2016.01) |

(52) U.S. Cl.
CPC ............ *A61K 8/0216* (2013.01); *A23K 20/00* (2016.05); *A23K 20/10* (2016.05); *A23K 20/158* (2016.05); *A23K 50/42* (2016.05); *A61K 8/553* (2013.01); *A61K 8/92* (2013.01); *A61Q 11/00* (2013.01)

(58) Field of Classification Search
CPC ........ A23K 1/16; A23K 1/164; A23K 1/1646; A23K 1/1853; A61K 8/0216; A61K 8/553; A61K 8/92; A61K 8/965; A61Q 11/00
See application file for complete search history.

(56) References Cited

U.S. PATENT DOCUMENTS

| | | | | |
|---|---|---|---|---|
| 5,296,209 | A * | 3/1994 | Simone | A23K 50/40 424/401 |
| 5,961,958 | A * | 10/1999 | Homola | A61K 8/41 106/35 |
| 7,390,520 | B2 * | 6/2008 | Dempsey | A23K 50/42 426/512 |
| 8,137,731 | B2 * | 3/2012 | Pater | A23K 50/48 426/512 |
| 2007/0065465 | A1 * | 3/2007 | Lees | A61K 39/092 424/244.1 |
| 2012/0231057 | A1 * | 9/2012 | Hack | A23L 1/304 424/401 |

\* cited by examiner

*Primary Examiner* — Snigdha Maewall
(74) *Attorney, Agent, or Firm* — Judy Jarecki-Black; Chad Kitchen; Merial Inc.

(57) ABSTRACT

The invention relates to a dental device and an edible pet chew. The dental device comprises a dental protection composition containing at least one barrier material, at least one activated phosphatidylcholine, and, optionally, mineral oil. The edible pet chew comprises a dental protection composition, gelatin, and, optionally, one or more humectants, one or more preservatives, one or more structure-providing components, and one or more flavoring ingredients, wherein the dental protection composition contains at least one barrier material, at least one phosphatidylcholine, and, optionally, mineral oil.

14 Claims, No Drawings

DENTAL DEVICE FOR INHIBITION OF PLAQUE, CALCULUS AND GINGIVITIS

BACKGROUND OF THE INVENTION

Humans as well as their pets, such as dogs and cats, are subject to dental health problems. These problems can be traced to the formation of bacterial plaque that forms on the exterior surface of teeth. Plaque is a gelatinous mass; a sticky film of bacteria, polysaccharides and salivary proteins that are not easily washed away. Plaque is now generally recognized as the main culprit in poor oral health. Bacteria that produce the acid for the caries process are held to the tooth surface by the plaque matrix as well as other bacterial agents that cause redness and swelling (i.e., gingivitis). The anaerobic microbial species that can proliferate when plaque is left undisturbed are also responsible for oral malodor and periodontitis that, if left untreated, can result in tooth loss.

Dental calculus, or tartar as it is commonly called, is the result of the thickening and hardening (mineralization) of dental plaque. Tartar, which is not easily removed, accumulates on the tooth surface, mainly at the gingival margin. Tartar is a hard mineral deposit containing predominantly calcium and phosphate, very tightly bound to the tooth surface. In addition to being unsightly and undesirable from an aesthetic standpoint, tartar deposits (i.e., mature calculus deposits) can, when they extend below the gingival margin, be constant sources of irritation of the gingiva and are therefore a contributing factor to gingivitis and its sequelae. Once mature and hardened tartar is formed, it can be difficult to remove and the assistance of a veterinary professional is typically sought. Thus, it is desirable to eliminate tartar once it occurs, and to prevent, or at least mitigate, new tartar buildup.

With regard to mammalian pets, such as cats and dogs, there is at least one dental product that is applied by a veterinarian or a veterinary assistant immediately following a professional dental cleaning that also includes a follow-up home-care product that is to be applied by the pet owner to the pet's teeth. This dental product utilizes a dental protection composition (OraVet®) that contains microcrystalline wax, mineral oil and hexetidine. While this product provides for protection against plaque adherence and related consequences, it has been found that many pet owners are unable or unwilling to place their fingers in or near the pet's teeth, and thus the follow-up care is neglected by the pet owner and the pet suffers from new plaque accumulation that can lead to gingivitis, periodontitis, caries, and other ill effects. Also, current commercial pet products that are edible, for example dog bones or cat treats, when chewed by the animal, typically do not provide sufficient mechanical surface cleaning to teeth to provide the amount of plaque removal that is necessary for optimal dental health. For instance, because animals like dogs and cats tend to bite or tear and then swallow their food without a great degree of chewing, it is difficult to obtain efficient contact between currently available pet products and the most important surfaces of teeth, especially molars, in the right and left sides of the mouth and mandibular as well as maxillary teeth.

There is therefore a need in the dental industry for a product that provides both enduring and improved oral care properties by virtue of the dental protection composition itself as well as a convenient and efficient manner in which to apply and distribute the dental protection composition to the teeth.

SUMMARY OF THE INVENTION

Embodiments of the invention are directed to dental devices for the inhibition of plaque, calculus and gingivitis comprising a dental protection composition containing at least one barrier material, at least one activated phosphatidylcholine ("APC"), and optionally containing mineral oil.

Embodiments of the invention are also directed to masticable devices for the inhibition of plaque, calculus and gingivitis comprising a dental protection composition containing at least one barrier material, at least one APC, and optionally containing mineral oil, wherein the application and distribution of the dental protection composition on the teeth is performed by the action of chewing.

DETAILED DESCRIPTION OF THE INVENTION

The foregoing will be apparent from the following more particular description of example embodiments of the invention.

An embodiment of the invention provides a dental device for the inhibition of plaque, calculus and gingivitis comprising a dental protection composition containing at least one barrier material, at least one APC, and, optionally, mineral oil.

The barrier material can be a microcrystalline wax, a polycrystalline wax, a natural wax, a synthetic wax, a silicone-based polymer, a fluoropolymer or combinations thereof. Examples of a natural wax include waxes of animal, vegetable or mineral origin. Animal waxes can be, for instance, beeswax, lanolin and spermaceti. Vegetable waxes can be, for instance, carnauba wax and candellila wax. Mineral waxes can be, for instance, petrolatum, ozokerite, montan, barnsdahl and ceresin. Examples of synthetic waxes include ethylenic polymers such as Carbowax®, polymethylene wax such as Paraflint®, and various other hydrocarbon types as obtained via Fisher-Tropsch synthesis. Examples of silicone-based polymers include polymethylalkylsiloxane, polydimethylsiloxane, poly(perfluoroalkylmethyl)siloxane, poly(methyl-3,3,3-trifluoropropyl)siloxane, and various aromatic phenyl-containing siloxanes. Examples of fluoropolymers include polytetrafluoroethylene (PTFE), fluorinated polyethylene-propylene (FEP), polyvinylidene fluoride (PVDF), and polyvinylfluoride (PVF).

In an embodiment of the invention, the barrier material can constitute about 52 to about 98 percent by weight of the dental protection composition. In a further embodiment of the invention, the barrier material can constitute about 63 to about 92 percent by weight of the dental protection composition. In yet a further embodiment, the barrier material can constitute about 74 to about 86 percent by weight of the dental protection composition, and may constitute about 80 percent by weight of the dental protection composition.

The activated phosphatidylcholine (APC) can be any phosphatidylcholine activated by the attachment of at least one divalent cation. Examples of divalent cations include calcium, magnesium, iron and barium. Examples of phosphatidylcholine include soybean lecithin, egg lecithin, rapeseed lecithin and sunflower lecithin.

In an embodiment of the invention, the APC can constitute about 2 to about 15 percent by weight of the dental protection composition. In a further embodiment of the invention, the APC can constitute about 3 to about 8 percent by weight of the dental protection composition. In yet a further embodiment, the APC can constitute about 4 to about 6 percent by weight of the dental protection composition, and may constitute about 5 percent by weight of the dental protection composition.

In an embodiment of the invention, the APC can be a calcium-activated soybean-lecithin. A first exemplary preparation method of calcium-activated soybean-lecithin is as follows. 10 grams of soybean lecithin (laboratory grade) sold by Fisher Scientific and 200 grams of water were mixed at room temperature for 30 minutes until a uniform dispersion was produced. To this mixture, 10 grams of 10% solution of calcium chloride ($CaCl_2.2H_2O$) sold by Fisher Scientific was added and vigorously mixed for 10 minutes. The result was a mixture in which calcium-activated soybean-lecithin product was uniformly dispersed. The mixture was filtered and the residual water was allowed to evaporate at an elevated temperature (105-110° C.). The dried filtrate was then dissolved in a warm mineral oil (105-110° C.) resulting in a clear 50% w/w solution of calcium-activated soybean-lecithin.

In an embodiment of the invention, a second exemplary preparation method of calcium-activated soybean-lecithin is as follows. 10 grams of soybean lecithin (laboratory grade) sold by Fisher Scientific or Arcos Organics was added to 100 grams of 2.5% solution of calcium chloride ($CaCl_2.2H_2O$) and vigorously mixed at room temperature for 2 hours. The resulting mixture was filtered and the residual water was allowed to evaporate at an elevated temperature (105-110° C.). The dried filtrate was then dissolved in hot (85° C.) microcrystalline wax at 5% w/w. 15% w/w of mineral oil was also added, resulting in a dental protection composition containing 5% w/w of calcium-activated soybean-lecithin, 15% w/w mineral oil and 80% w/w microcrystalline wax.

In another embodiment of the invention, the APC can be a magnesium-activated soybean-lecithin. An exemplary preparation method of magnesium-activated soybean-lecithin is as follows. 10 grams of soybean lecithin (laboratory grade) sold by Fisher Scientific and 200 grams of water were mixed at room temperature for 30 minutes until a uniform dispersion was produced. To this mixture, 10 grams of 15% solution of magnesium chloride ($MgCl_2.6H_2O$) sold by Fisher Scientific was added and vigorously mixed for 10 minutes. The result was a mixture in which magnesium-activated soybean-lecithin product was uniformly dispersed. The mixture was filtered and the residual water was allowed to evaporate at an elevated temperature (105-110° C.). The dried filtrate was then dissolved in a warm mineral oil (105-110° C.) resulting in a clear 50% w/w solution of magnesium-activated soybean-lecithin.

In another embodiment of the invention, calcium- and magnesium-activated lecithin could be prepared using the selected barrier material, in liquid form, to dissolve the dried filtrate of calcium- or magnesium-activated lecithin. Use of the selected barrier material to dissolve the dried filtrate can, if desired, proceed without the use of mineral oil.

In an embodiment of the invention, the dental protection composition may contain mineral oil. In a further embodiment of the invention, the mineral oil can constitute no more than about 40 percent by weight of the dental protection composition. In yet a further embodiment, the mineral oil can constitute about 5 to about 30 percent by weight of the dental protection composition, and may constitute about 10 to about 20 percent by weight of the dental protection composition. In an even further embodiment of the invention, the mineral oil can constitute about 15 percent by weight of the dental protection composition.

An embodiment of the invention includes a dental device that may further comprise one or more of the following, in addition to the dental protection composition: a source of fluoride (e.g. sodium fluoride, potassium fluoride, tin fluoride, zinc fluoride, organic fluorides such as long-chained aminofluorides, fluorosilicates, fluorophosphates and fluorozirconates), an antibiotic (e.g. penicillin, polymyxin B, vancomycin, kanamycin, erythromycin, niddamycin, metronidazole, spiramycin and tetracycline), an antimicrobial agent (e.g. those described in U.S. Pat. No. 5,961,958, and a flavoring ingredient (e.g. oils and aromatic/flavorant materials such as cinnamon, lemon, lime, orange, spearmint, peppermint, clove and almond). Examples of long-chained aminofluorides include oleylaminofluoride, cetylaminofluoride and ethanolaminohydrofluoride. Examples of fluorosilicates include potassium hexafluorosilicate and sodium hexafluorosilicate. Examples of fluorophosphates include ammonium, sodium, potassium, magnesium and calcium fluorophosphate. Examples of fluorozirconates include sodium, potassium and tin fluorozirconate. Examples of antimicrobial agents include amine-free compounds (e.g. halogenated salicylanilides, halogenated diphenyl ethers, halogenated carbanilides and phenolic compounds), amine-containing compounds (e.g. quaternary amines), and nitroparaffin-derived heterocyclic compounds (e.g. monocyclic oxazolidines, bicyclic oxalidines, polymeric bicyclic oxalidines, 1,3-dioxanes, oxazolines, oxazolidinones and hexahydropyrimidines).

In a further embodiment of the invention, the dental device for the inhibition of plaque, calculus and gingivitis comprises a dental protection composition comprising about 52 to about 98 percent by weight of at least one barrier material, about 2 to about 15 percent by weight of at least one APC, and 0 to about 40 percent by weight of mineral oil.

In a further embodiment of the invention, the dental device for the inhibition of plaque, calculus and gingivitis comprises a dental protection composition comprising about 80 percent by weight of at least one barrier material, about 5 percent by weight of at least one APC, and about 15 percent by weight of mineral oil.

In a further embodiment of the invention, the dental device for the inhibition of plaque, calculus and gingivitis comprises a dental protection composition comprising about 80 percent by weight of microcrystalline wax, about 5 percent by weight of calcium-activated soybean lecithin, and about 15 percent by weight of mineral oil.

The dental device of the invention may be applied to dental surfaces via a myriad of applicators, for instance, brushes, dental floss, dental tape, interdental appliances, swabs, sticks, toothpicks, toothpaste, masticable devices (including chewing gums and edible chewing matrices), and other applicators or methods of application by which semisolid or solid materials may be brought into contact with dental surfaces.

The dental device embodiments of the invention may be applied by an untrained consumer, a dentist or dental assistant, a pet owner, a veterinarian or veterinary assistant, and other individuals, and may be applied to oneself or to others. A variety of applicators can be used for the embodiments of the invention by those using the embodiments for the various uses. Certain applicators may be selected by a user for certain purposes, for example self-application and application to another. Certain applicators may be chosen for use for application to a pet (e.g. dog or cat), for instance masticable devices such as edible chewing matrices. Applicators other than masticable devices can also be used for application to a pet.

An embodiment of the invention provides a masticable device for the inhibition of plaque, calculus and gingivitis comprising a dental protection composition containing at least one barrier material, at least one APC, and optionally containing mineral oil, wherein the application or deposition of the dental protection composition on the teeth is performed by the action of chewing.

Typical masticable devices include products such as chewing gums or the like, which are traditionally not intended for ingestion, and edible chewing matrices such as chewy candies, treats and other food-based items that are typically intended for ingestion. When considering a human user, one may choose to select the form of the masticable device to be a traditional chewing gum or candy. When considering an animal that is a pet user, such as a dog or cat, one may choose to select the form of the masticable device to be a chewable rope or edible pet chew or edible pet treat.

An embodiment of the invention provides an easily-digestible edible pet chew that promotes oral health and prevents bad breath in animals. A further embodiment of the invention provides a pet chew that is specifically formulated using the above-described dental protection composition in a gelatin-based composition to produce a soft chew that promotes chewing and is quickly and completely digested by a pet.

In an embodiment of the invention, in addition to the dental protection composition and gelatin, which are present in the pet chew in an amount of about 10 to about 25 weight percent and about 15 to about 35 weight percent respectively, the pet chew may further contain one or more humectants, one or more preservatives, one or more structure-providing components, one or more flavoring ingredients, one or more anti-odor ingredients, or combinations thereof.

Potential humectants include glycerin, sorbitol, polydextrose and propylene glycol. In an embodiment of the invention, the humectants can constitute about 1 to about 5 weight percent of the pet chew.

Preservatives that may be used are, for example, potassium sorbate, sorbic acid (and its salts), benzoic acid (and its salts), calcium propionate, and sodium nitrate. In an embodiment of the invention, the preservatives can constitute about 0.1 to about 1.0 weight percent of the pet chew.

The structure-providing component can include abrasive agents, for example, coconut fibers, powdered cellulose, cellulose fibers such as hemp, cotton, coir and agave, and animal-based fibers such as silk, wool, alpaca and mohair.

The structure-providing component may be the same as one or more of the flavoring ingredients. For instance, the flavoring ingredients of shredded beef jerky and dehydrated sweet potatoes (see below) are examples of flavoring ingredients that also provide structure to the pet chew and thus are ingredients that are both a structure-providing component and a flavoring ingredient at the same time.

In an embodiment of the invention, the structure-providing components can constitute 0 to about 45 weight percent of the pet chew.

The various flavoring ingredients that may be incorporated into the edible pet chew include ingredients such as beef liver powder, bacon bits, liver, fat, garlic, onion, sweet potatoes (including dehydrated sweet potatoes), anise, horsemeat, lamb, beef (including shredded beef jerky), cheese, fish, chicken, turkey and yeast. In an embodiment of the invention, the flavoring ingredients can constitute about 10 to about 45 weight percent of the pet chew; however, a portion of this weight percent may be attributable to the structure-providing components as well.

When the edible pet chew includes one more of the structure-providing components, the unique combination of the soft texture of the gelatin-based composition and the infusion with structure-providing components encourages the animal to chew the treat longer without the pet chew breaking apart and being swallowed prematurely. This elongated chewing time allows for increased deposition and distribution of the dental protection composition on the teeth and the texture of the structure-providing components such as the abrasive agents gently abrades the teeth to further eliminate tartar and plaque while the animal is chewing. The structure-providing components, such as the abrasive agents, also function to remove surface detritus on teeth including for example mucus, so that the dental protection composition is more readily deposited and distributed without inhibition by the detritus, mucus, etc.

A further embodiment of the invention includes an edible pet chew containing a core material that can be hard in nature or soft in nature. For example, the edible pet chew could contain rawhide as a core material that is encased in or coated with the above-noted formulations constituting the edible pet chew. Potential core materials that are hard in nature include rawhide and bully sticks or twists. Potential core materials that are soft in nature include nylon sticks and natural rubber.

The edible pet chews of the invention can be formed using extrusion molding or an injection molding process that provides significant control over the shape and texture of the pet chews. The edible pet chew can be shaped like a bone to appeal to a dog or shaped like a worm and optionally infused with catnip to appeal to a cat. Any shape or geometry may be applied to the edible pet chew as desired.

After the extrusion or injection molding process, the pet chews are cured for an extensive amount of time, for example from several hours to five days (at room temperature), to aid in the evaporation of just the right amount of moisture such that the pet chew retains its malleability and does not become too hard. In an embodiment of the invention, the curing process results in a moisture content of about 5 to about 30% (by weight).

In an embodiment of the invention, the edible pet chew has a moisture content of about 5% to about 30% (by weight) and comprises about 10% to about 25% by weight of the above-described dental protection composition, about 15% to about 35% by weight of gelatin, about 1% to about 5% by weight of humectant, about 0.1% to about 1.0% by weight of preservatives, 0% to about 45% by weight of structure-providing component, and about 10% to about 45% by weight of flavoring ingredients.

In another embodiment of the invention, the edible pet chew has a moisture content of about 5% to about 30% (by weight) and comprises about 10% to about 25% by weight of the above-described dental protection composition, about 15% to about 35% by weight of gelatin, about 1% to about 5% by weight of vegetable glycerin, about 0.1% to about 1.0% by weight of potassium sorbate, and about 10% to about 45% by weight of a mixture of shredded beef jerky and dehydrated sweet potatoes (which also constitute structure-providing components).

In yet another embodiment of the invention, the edible pet chew has a moisture content of about 17% (by weight) and comprises about 14% by weight of the above-described dental protection composition, about 21% by weight of gelatin, about 4% by weight of vegetable glycerin, about 0.8% by weight of potassium sorbate, about 14% by weight of shredded beef jerky and about 29% by weight of dehydrated sweet potatoes.

EXAMPLE 1

Edible Pet Chew

An exemplary edible pet chew was produced according to the following. In a first container, 500 grams of gelatin (from Burman Industries), 400 grams of water, 100 grams of vegetable glycerin (from Essential Depot Co.), and 20 grams of potassium sorbate (from Fisher Scientific) were mixed well. In a second container, 700 grams of dehydrated sweet potatoes (from Mother Earth Products), 350 grams of shredded beef jerky (from Jack Link's Co.), and 350 grams of a dental protection composition (80 wt % microcrystalline wax, 15 wt % mineral oil and 5 wt % calcium-activated soybean-lecithin; using the above-described "second exemplary preparation method of calcium-activated soybean-lecithin") were mixed together. Both containers were placed in a warm oven (85° C.) for 60 minutes. After heating, both mixtures were combined and mixed together resulting in a formulation containing well distributed ingredients. The warm mixture was then placed in a mold and cooled to a temperature below 40° C. The final product was cut into 50 separate edible pet chews and allowed to dry at room temperature for 3 days to reach a stable weight.

EXAMPLE 2

Edible Pet Chew

An exemplary edible pet chew can be produced according to the following. In a first container, 400 g of water, 500 g of gelatin, 100 g of glycerol, 20 g of potassium sorbate, 10g of calcium chloride and 20 g of lecithin are combined. The contents of the first container are then heated to about 85° C. and stirred vigorously for a minimum of 1 hour. 350 g of liquefied microcrystalline wax containing 15% of mineral oil is then added and the resulting mixture is stirred again for 1 hour. In a second container, 350 g of shredded beef jerky and 700 g of dehydrated sweet potatoes are combined and heated to about 85° C. The contents of the first and second containers are then combined and thoroughly mixed together resulting in a formulation containing well distributed ingredients. The resulting mixture is then molded (e.g., extrusion or injection) and cooled to a temperature below 40° C.

Testing Procedure

A first group of 15 dogs was fed only Purina Dog Chow® at meal times for 28 days (see column titled "Purina Dog Chow" in Tables 1-3 below). A second group of 15 dogs was also fed Purina Dog Chow® at meal times for 28 days but also received an application of just the dental protection composition of Example 1 (i.e. composition of 80 wt % microcrystalline wax, 15 wt % mineral oil and 5 wt % calcium-activated soybean-lecithin) ("ProVSeal Barrier Sealant") along the gingival margins on the buccal sides of the maxillary and mandibular teeth on both sides of the mouth on day zero and also received a pet chew of Example 1 once a day for the 28 days (see column titled "ProVSeal Barrier Sealant/ProVSeal Chew" in Tables 1-3 below). After the 28 day period was completed, plaque scores, gingivitis scores and calculus scores were obtained for the left maxilla, left mandible, right maxilla and right mandible of each of the 30 dogs. From those scores, mean left, mean right and mean mouth scores were calculated for each group of dogs. The results were as follows.

Results

TABLE 1

Day 28 Plaque Reduction Comparisons

|  | ProVSeal Barrier Sealant/ProVSeal Chew | Purina Dog Chow | % Reduction |
| --- | --- | --- | --- |
| Mean Left | 0.7 | 1.1 | 40.5 ** |
| Mean Right | 0.6 | 1.1 | 45.3 ** |
| Mean Mouth | 0.6 | 1.1 | 42.8 ** |

TABLE 2

Day 28 Gingivitis Reduction Comparisons

|  | ProVSeal Barrier Sealant/ProVSeal Chew | Purina Dog Chow | % Reduction |
| --- | --- | --- | --- |
| Mean Left | 0.2 | 0.3 | 52.4 * |
| Mean Right | 0.2 | 0.4 | 42.0 |
| Mean Mouth | 0.2 | 0.3 | 47.0 |

TABLE 3

Day 28 Calculus Reduction Comparisons

|  | ProVSeal Barrier Sealant/ProVSeal Chew | Purina Dog Chow | % Reduction |
| --- | --- | --- | --- |
| Mean Left | 0.6 | 1.7 | 62.9 ** |
| Mean Right | 0.8 | 1.8 | 57.2 ** |
| Mean Mouth | 0.7 | 1.7 | 60.0 ** |

* t-Test statistically significant ($P < 0.05$) compared to Group 1
** t-Test statistically significant ($P < 0.01$) compared to Group 1

As can be seen from the above results, the combined use of an inventive dental device (~80 wt % microcrystalline wax, ~5 wt % calcium-activated soybean-lecithin, ~15 wt % mineral oil) and an inventive edible pet chew (~17 wt % moisture, ~14 wt % dental protection composition, ~21 wt % gelatin, ~4 wt % vegetable glycerin, ~0.8 wt % potassium sorbate, ~14 wt % shredded beef jerky, ~29 wt % dehydrated sweet potatoes) resulted in a 42.8% reduction in plaque, a 47.0% reduction in gingivitis, and a 60.0% reduction in calculus. The results for reduction of calculus and plaque are highly statistically significant.

An embodiment of the invention also provides a chewable rope that provides a long lasting, inexpensive and effective means for assisting pets and their owners to maintain the pet's good oral health by allowing for a simple and practical method of applying or depositing a dental protection composition to the teeth of pets.

In an embodiment of the invention, the chewable rope, which can be made from nylon, cotton or hemp for example, is impregnated with a dental protection composition in the amount of from about 10% to about 25% by weight. The dental protection composition may be, for example, the same as discussed above. In a further embodiment, a flavoring, which encourages chewing by an animal, can also be incorporated into the dental protection composition prior to rope impregnation. Exemplary flavoring can include catnip or cod liver oil for pets such as cats, or the flavoring can include a combination of cod liver oil, beef liver and beef broth for pets such as dogs. In an embodiment of the invention, these flavorings can be incorporated separately into the rope, and in another embodiment, the dental protection composition can be impregnated with one or more of the flavorings prior to the rope impregnation. In an embodiment of the invention, these flavorings in the dental protection composition can vary between about 5% and about 15% by weight.

In an embodiment of the invention, the dental protection composition, optionally containing one or more flavorings, can be applied to chewable rope by spraying in a spray chamber or by passing the chewable rope through a bath of the liquid form of the dental protection composition. In an embodiment, the liquid form of the dental protection composition can be attained by heating said composition to a temperature within the range of about 75 to about 80° C. After impregnation of the chewable rope with the dental protection composition optionally containing one or more flavorings, the impregnated rope is then passed through a drying and cooling station.

A further embodiment of the invention includes a chewable rope that comprises chewable rope as a core material and also comprises any one of the above-described edible pet chew formulations as a coating surrounding the rope core.

It is envisioned by the inventors that a human-based application of the invention is possible. As such, other potential masticable devices of the invention include, for example, chewing gum and candy. Rather than an edible pet chew that is formulated for application to a pet and with pet appeal in mind, an embodiment with human appeal and for application to human teeth has been foreseen. Embodiments for human use would utilize the above-described dental device of the invention as the foundation, but those skilled in the art would be able to readily ascertain which changes would be desirable when considering the human-use nature of such embodiments.

The term "about" as used in the above description is intended to refer to a difference in value of up to 10 percent, positively or negatively. For example, "about 50" would mean 50 plus or minus a maximum of 10 percent. In other words, "about 50" refers to no less than 45 and no more than 55.

While this invention has been particularly shown and described with references to example embodiments thereof, it will be understood by those skilled in the art that various changes in form and details may be made therein without departing from the scope of the invention encompassed by the appended claims.

What is claimed is:

1. An edible pet chew for the inhibition of plaque, calculus and gingivitis, which promotes elongated chewing time and is quickly and completely digested by a pet, comprising:
   about 10% to 30% by weight of a dental protection composition, comprising 1% to 3% by weight of a divalent cation-activated lecithin transfer agent and 82% to 99% by weight of a barrier material comprising a microcrystalline wax;
   21% to 35% by weight of gelatin,
   optionally, one or more humectants,
   optionally, one or more preservatives,
   3% to about 40% by weight of one or more structure-providing components selected from coconut fiber, powdered cellulose, hemp, cotton, coir, agave, silk, wool, alpaca, mohair, shredded beef jerky, and comprises dehydrated sweet potato, and
   optionally, flavoring ingredients, wherein the dental protection composition optionally comprises up to about 15% by weight mineral oil; and
   wherein the edible pet chew has a moisture content of 15% to 25% by weight; and
   whereby the elongated chewing time provides for the application or deposition of the dental protection composition on the pet's teeth, leading to the inhibition of plaque, calculus and gingivitis.

2. The edible pet chew of claim 1, wherein the dental protection composition is present in an amount of 10 to about 25 percent by weight of the edible pet chew; and wherein the barrier material is present in an amount of 97% to 99.75% by weight of the dental protection composition.

3. The edible pet chew of claim 1, wherein the gelatin is present in an amount of 21 to about 35 percent by weight of the edible pet chew.

4. The edible pet chew of claim 1, wherein the one or more humectants are present in the amount of about 1 to about 5 weight percent of the pet chew, and wherein the humectants are selected from the group consisting of glycerin, sorbitol, polydextrose and propylene glycol.

5. The edible pet chew of claim 1, wherein the one or more humectants comprise glycerin and are present in an amount of about 4 percent by weight of the edible pet chew.

6. The edible pet chew of claim 1, wherein the one or more preservatives are present in an amount of about 0.1% to about 1.0% by weight, and wherein the preservatives are selected from the group consisting of potassium sorbate, sorbic acid, benzoic acid, calcium propionate, sodium nitrate, and disodium EDTA.

7. The edible pet chew of claim 1, wherein the one or more preservatives are present in an amount of about 0.1 to about 1.0 percent by weight of the edible pet chew.

8. The edible pet chew of claim 1, wherein the one or more structure-providing components comprises dehydrated sweet potato.

9. The edible pet chew of claim 1, wherein the one or more structure-providing components are present in an amount of about 40 percent by weight of the edible pet chew.

10. The edible pet chew of claim 1, wherein the one or more flavoring ingredients are selected from the group consisting of beef liver powder, bacon bits, liver, fat, garlic, onion, sweet potato, anise, horsemeat, lamb, beef, cheese, fish, chicken, turkey and yeast.

11. The edible pet chew of claim 1, wherein the one or more flavoring ingredients are present and are present in an amount of about 10 to about 45 percent by weight of the edible pet chew.

12. An edible pet chew having a moisture content of about 17% by weight and comprising:
    about 14% by weight of a dental protection composition, wherein the dental protection composition comprises about 80 percent by weight of microcrystalline wax, about 5 percent by weight of calcium-activated soybean lecithin, and
    about 15 percent by weight of mineral oil,
    about 21% by weight of gelatin,
    about 4% by weight of vegetable glycerin,
    about 0.8% by weight of potassium sorbate,
    about 14% by weight of shredded beef jerky, and
    about 29% by weight of dehydrated sweet potatoes.

13. The chew of claim 1, produced according to the following process:
    a) combining in a first container gelatin, water, vegetable glycerin and optionally potassium sorbate;
    b) combining in a second container dehydrated sweet potatoes, shredded beef jerky and a dental protection composition; wherein the dental protection composition comprises about 80 wt% microcrystalline wax, 15 wt% mineral oil and 5 wt% divalent cation activated soybean-lecithin;
c) placing both the first and second containers in a warm oven to heat the containers and their contents;
d) combining the contents of the first and second containers to product a formulation containing well distributed ingredients;
e) placing the warm formulation in a mold;
f) cooling the formulation to a temperature below about 40° C.;
g) cutting the molded product into edible pet chews; and
h) allowing the chews to dry to reach a stable weight.

14. The chew of claim 1, produced according to the following process:
a) combining in a first container water, gelatin, glycerol, optionally potassium sorbate, calcium chloride and lecithin are combined;
b) heating the contents of the first container to about 85° C. and stirring vigorously for a minimum of 1 hour;
c) adding liquefied microcrystalline wax containing about 15% of mineral oil to the resulting mixture from step (b);
d) stirring the resulting mixture from step (c) for at least about 1 hour;
e) combining in a second container shredded beef jerky and dehydrated sweet potatoes and heating;
f) combining and thoroughly mixing the contents of the first and second containers to make a formulation containing well distributed ingredients;
g) molding, extruding or injecting and cooling to produce the edible chew.

* * * * *